(12) United States Patent
Isayama et al.

(10) Patent No.: US 11,633,209 B2
(45) Date of Patent: Apr. 25, 2023

(54) METHOD FOR FORMING ACCESS ROUTE TO BILE DUCT AND TREATMENT METHOD

(71) Applicants: Hiroyuki Isayama, Tokyo (JP); OLYMPUS MEDICAL SYSTEMS CORP., Tokyo (JP)

(72) Inventors: Hiroyuki Isayama, Tokyo (JP); Tomohiko Mamiya, Kawasaki (JP); Yutaka Yanuma, Tokyo (JP)

(73) Assignees: Hiroyuki Isayama, Tokyo (JP); OLYMPUS MEDICAL SYSTEMS CORP., Tokyo (JP)

( * ) Notice: Subject to any disclaimer, the term of this patent is extended or adjusted under 35 U.S.C. 154(b) by 368 days.

(21) Appl. No.: 17/081,270

(22) Filed: Oct. 27, 2020

(65) Prior Publication Data
US 2022/0125478 A1   Apr. 28, 2022

(51) Int. Cl.
*A61B 17/34*    (2006.01)

(52) U.S. Cl.
CPC ...... *A61B 17/3423* (2013.01); *A61B 17/3403* (2013.01); *A61B 17/3478* (2013.01); *A61B 17/3496* (2013.01); *A61B 2017/3413* (2013.01)

(58) Field of Classification Search
CPC ............ A61B 17/3403; A61B 17/3423; A61B 17/3478; A61B 17/3496; A61B 2017/3413
See application file for complete search history.

(56) References Cited

U.S. PATENT DOCUMENTS

| 2009/0069822 A1* | 3/2009 | Takahashi | A61B 17/068 606/139 |
| 2009/0318831 A1* | 12/2009 | Aoki | A61B 1/05 600/106 |
| 2013/0325038 A1* | 12/2013 | Sato | A61B 17/3468 606/139 |
| 2018/0280669 A1* | 10/2018 | Shlomovitz | A61M 27/002 |

FOREIGN PATENT DOCUMENTS

| JP | 2013-507185 A | 3/2013 |
| WO | 2011-044192 A1 | 4/2011 |

* cited by examiner

*Primary Examiner* — Nicholas W Woodall
(74) *Attorney, Agent, or Firm* — Oliff PLC (57) ABSTRACT

In a method of forming an access route to the bile duct, a needle is introduced into a duodenum, and the introduced needle is pierced into an oral side projection of a duodenal papilla, which is located at an oral position than an opening of the duodenal papilla. The tip of the pierced needle is made to reach the inside of the bile duct to form a tunnel communicating the duodenum and the bile duct, and a treatment device is inserted into the formed tunnel.

12 Claims, 11 Drawing Sheets

METHOD FOR FORMING ACCESS ROUTE TO BILE DUCT AND TREATMENT METHOD

BACKGROUND

Technical Field

The present invention relates to a method for forming an access route to a bile duct, and more specifically, a method for forming a route to access a bile duct from within a duodenum without touching an opening of a duodenal papilla. A treatment method using the method for forming an access route is also mentioned.

Background Art

Endoscopic retrograde cholangiopancreatography (ERCP) remains a challenging procedure. Post-ERCP pancreatitis is a frequent complication and can be severe or fatal.

In post-ERCP pancreatitis, the opening of the duodenal papilla, the common duct after the bile duct and the pancreatic duct merge, the ostium of the pancreatic duct, which is the confluence of the pancreatic duct and the bile duct, or the like are stimulated when accessing the bile duct. It is thought that this causes papilla edema or papilla sphincter spasm, resulting in impaired outflow of pancreatic fluid (obstruction of the pancreatic duct opening). Therefore, access to the bile duct without touching the ostium of the pancreatic duct, the opening of the duodenal papilla, and the common duct may suppress post-ERCP pancreatitis.

Published Japanese Translation No. 2013-507185 of the PCT International Publication discloses a technique in which a needle is inserted into the duodenum and the common bile duct from within the duodenum, and a stent is placed in the formed tunnel. The stent is placed so that it is exposed in the abdominal cavity, and a route is formed through which bile is drained from the common bile duct without passing through the duodenal papilla.

SUMMARY

The present invention is a method for forming an access route to a bile duct, the method including: introducing a needle into a duodenum; piercing an oral side projection of a duodenal papilla with the needle, the oral side projection being located at an oral position than an opening of the duodenal papilla; forming a tunnel communicating the duodenum and the bile duct, by progressing a tip of the needle into the bile duct; and inserting a treatment device into the tunnel.

DETAILED DESCRIPTION OF THE PREFERRED EMBODIMENTS

An embodiment of the present invention will be described with reference to FIGS. 1 to 14.

First, a flexible endoscope having a flexible insertion portion is inserted into the luminal organ through the target's mouth or nose, and the distal end portion is moved to the vicinity of the duodenal papilla.

Figure 1:
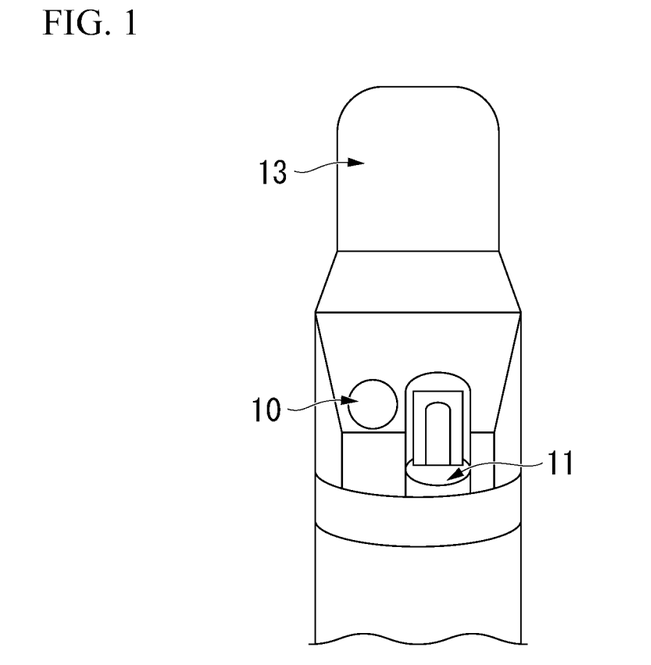
FIG. 1 is a diagram showing an example of an endoscope used in an access route forming method of the present invention.
Figure 2:
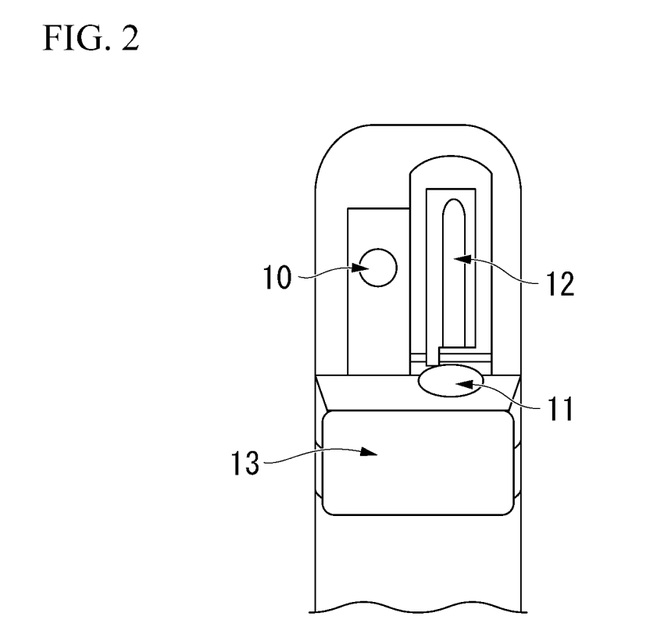
FIG. 2 is a diagram showing another example of the endoscope.

The endoscope used in the present embodiment is a duodenal endoscope that includes an optical observation part 10 and an ultrasound vibrator 13 and is capable of optical observation and ultrasound observation. There are two types of such endoscope. FIG. 1 shows a first type, in which the ultrasound vibrator 13 is located forward of the outlet 11 of the treatment device channel. FIG. 2 shows a second type, in which the ultrasound vibrator 13 is located more proximally than the outlet 11 of the treatment device channel. Both of the first type and the second type can be used for the method for forming an access route to the bile duct according to the present embodiment (hereinafter, simply referred to as "route forming method").

Figure 3:
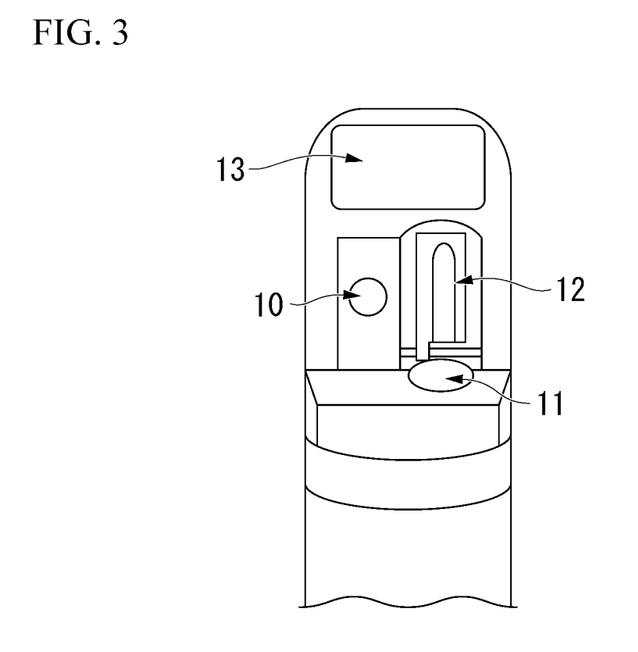
FIG. 3 is a diagram showing another example of the endoscope.

In an endoscope, it is desirable that the visual field direction of the optical observation part 10 is 90° or more in the distal end direction relative to the endoscope axis (longitudinal axis of the elongated insertion portion) (the visual field direction of the optical observation part 10 is directed proximally in the endoscope axis). In addition, it is desirable to have a forceps raising table that directs the treatment device 90° or more in the distal end direction relative to the endoscope axis (directs the treatment device proximally in the endoscope axis). In the endoscope shown in FIG. 2, the visual field direction of the optical observation part 10 is 90° or more in the distal end direction relative to the endoscope axis (the visual field direction of the optical observation part 10 is directed proximally in the endoscope axis), and the raising table 12 allows the treatment device coming out of the outlet 11 to be directed 90° or more in the distal end direction relative to the endoscope axis (directed proximally in the endoscope axis). The endoscope shown in FIG. 3 is of the first type, but the arrangement and orientation of the optical observation part 10 are different from those of the endoscope shown in FIG. 1, and the visual field direction of the optical observation part 10 is directed 90° or more in the distal end direction relative to the endoscope axis (directed proximally in the endoscope axis). Further, the raising table 12 can direct the treatment device coming out of the outlet 11 to 90° or more in the distal end direction relative to the endoscope axis (directed proximally in the endoscope axis).

Next, the duodenal papilla is imaged in the field of view of the optical observation part 10 of the endoscope. This operation is the same as the operation in a general ERCP or the like, and is performed by appropriately combining an advance/retreat operation, a bending operation, a twisting operation, and the like of the endoscope. When imaging the duodenal papilla in the field of view, it is desirable to position the duodenal papilla in front (center) of the optical image.

Next, water is supplied into the duodenum, and water is stored in the duodenum where the distal end of the endoscope is located.

Water can be supplied by using the water supply function of the endoscope, a syringe passed through the treatment device channel of the endoscope, or the like.

Figure 4:
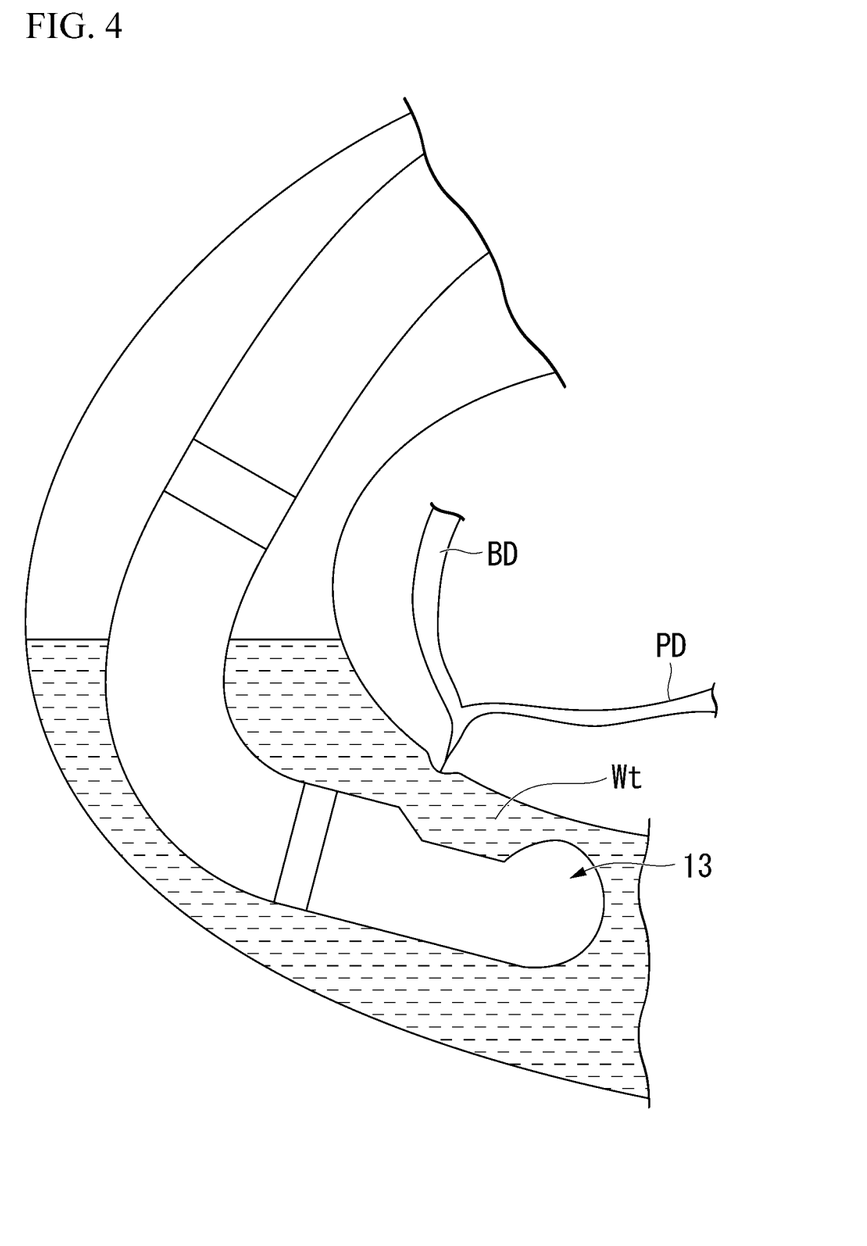
FIG. 4 is a diagram showing one process of the access route forming method according to an embodiment of the present invention.

As shown in FIG. 4, water is stored to such an extent that the space between the ultrasound vibrator 13 and the duodenal wall and the space between the endoscopic treatment device channel outlet and the duodenal wall are filled with water Wt. As a result, an environment is prepared in which the bile duct BD, the pancreatic duct PD, and the sheath and needle (described later) protruding from the treatment device channel can be imaged in an ultrasound endoscopic image using the ultrasound vibrator 13.

The posture of the patient when storing water in the duodenal area is preferably the prone position or the left lateral decubitus position, and may be the supine position. The prone position is a common posture in ERCP and can be easily performed.

Balloons may be used to store water, if desired. It is possible to prevent water from moving to the stomach side by introducing the endoscope into the duodenum with the endoscope passed through an overtube with a balloon attached to the outer circumference and inflating the balloon in the duodenum closer to the mouth than the duodenal papilla.

After storing the water, the operator operates the ultrasound vibrator 13 to acquire an ultrasound image, and confirms that the bile duct and pancreatic duct can be imaged. The water to be stored may be degassed water or may contain an electrolyte or the like such as a physiological saline solution.

Once the environment for imaging the ultrasound image is ready, the operator confirms whether the bile duct/the pancreatic duct is imaged in the ultrasound image before the insertion position is aligned on the optical image.

Next, the operator inserts the puncture device into the treatment device channel from the entrance of the treatment device channel provided in the operation part of the endoscope.

Figure 5:
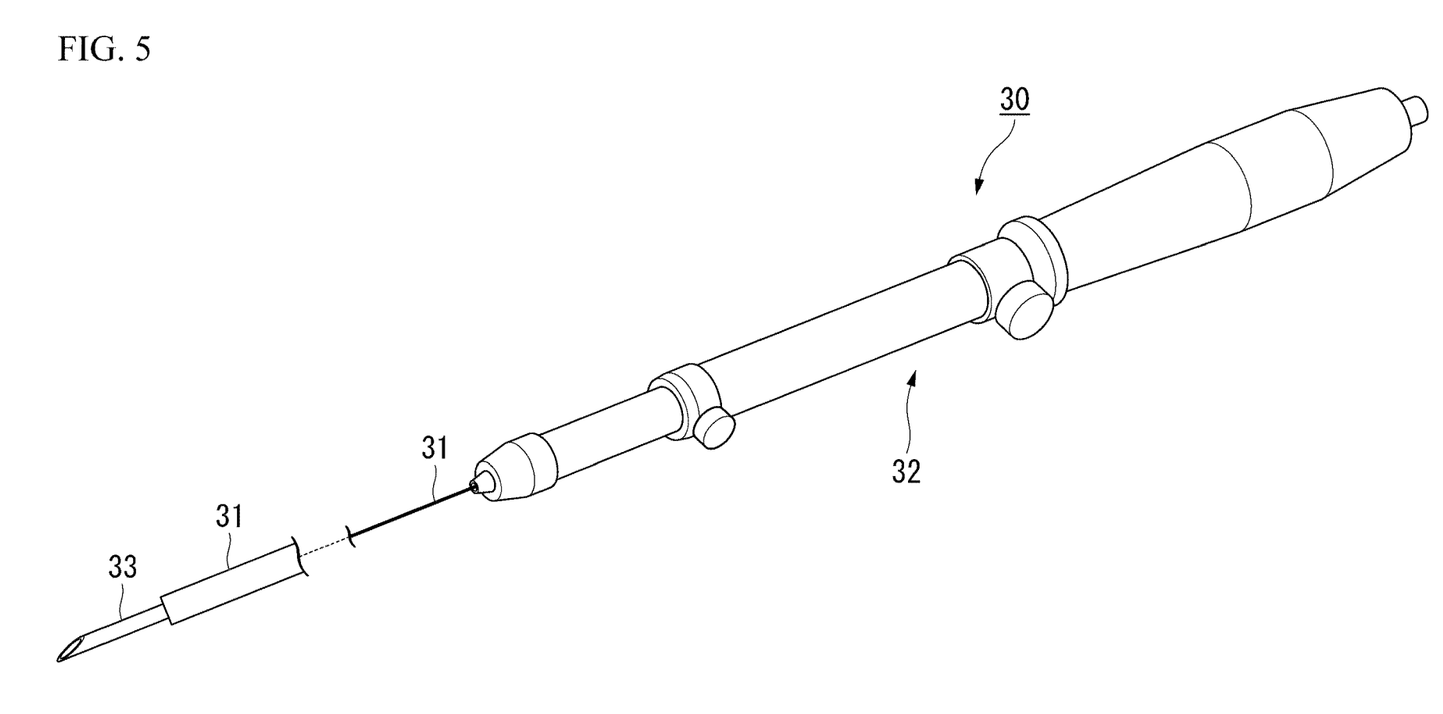
FIG. 5 is a diagram showing an example of a puncture device used in the access route forming method of the present invention.

FIG. 5 shows an example of the puncture device. The puncture device 30 shown in FIG. 5 includes an elongated sheath 31, an operation part 32 attached to the sheath 31, and a needle tube 33 connected to the operation part 32. The needle tube 33 is passed through the sheath 31, and by operating the operation part 32, the needle tube 33 can be protruded from the sheath 31 or stored in the sheath 31.

The needle tube 33 may have one or more dimples having a recessed outer surface at the distal end. In this case, the ultrasound waves are easily reflected, and the position of the needle can be easily confirmed on the ultrasound image.

When the puncture device 30 is inserted into the endoscopic channel, the operator positions the distal end of the sheath 31 near the exit of the treatment device channel. When the endoscope has the raising table, the raising table may be raised in advance and the distal end of the sheath 31 may be inserted until it reaches the raising table. When the sheath 31 reaches the vicinity of the raising table, the operation part 32 may be fixed to the entrance of the treatment device channel.

The operator operates the endoscope and the puncture device to position the distal end of the sheath 31 within the field of view of the optical observation part 10. In a case where the endoscope has the raising table, the raising table may be operated as needed. At this point, as in the example shown in FIG. 6, the distal end of the needle tube 33 introduced into the duodenum is still in the sheath 31, and the opening Po and the oral side projection Op of the duodenal papilla and the distal end of the sheath 31 are imaged in the field of view.

Figure 6:
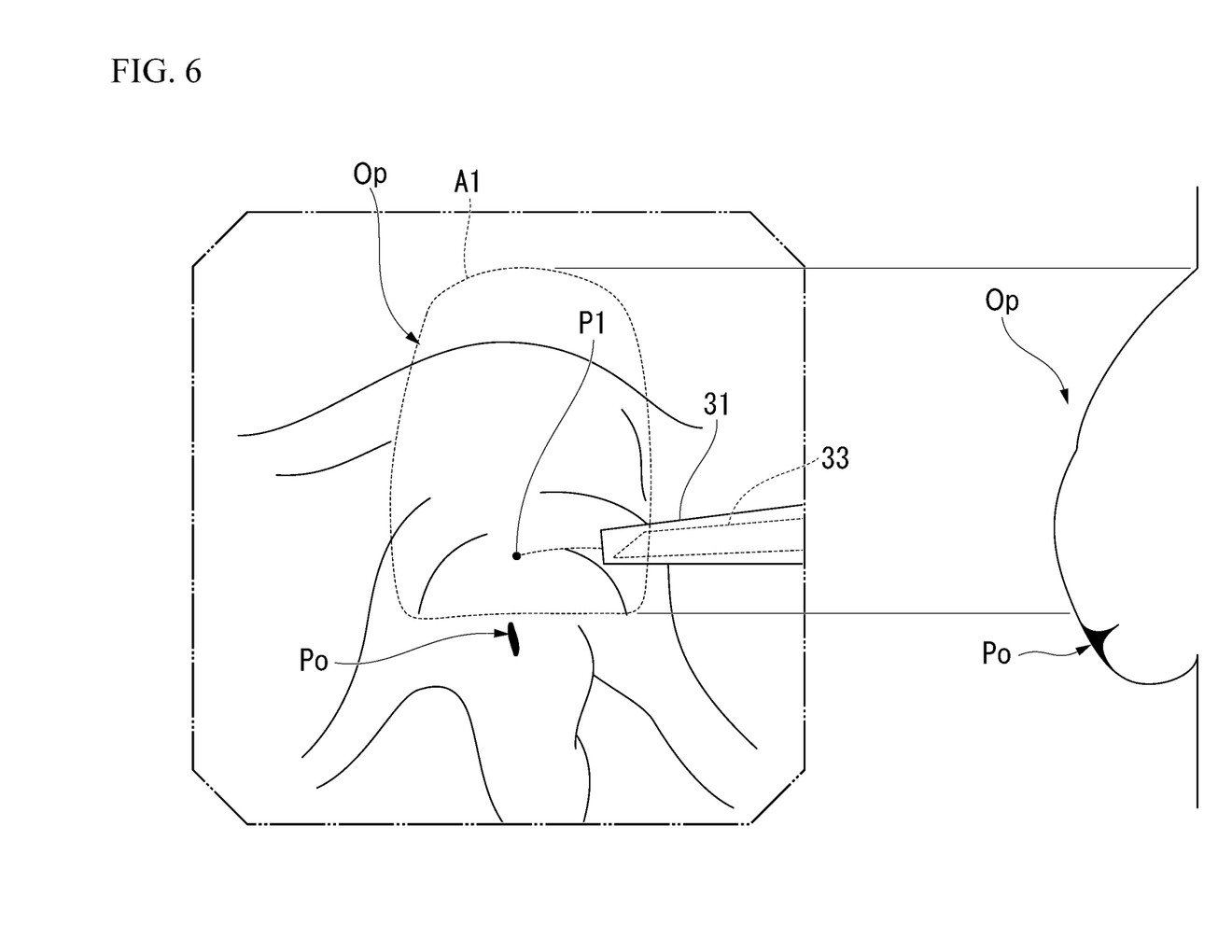
FIG. 6 is a diagram showing one process of an access route forming method according to an embodiment.

The operator estimates the position P1 on the duodenal surface that coincides with the extension line of the sheath 31 while viewing the image as shown in FIG. 6 with an endoscope. That is, the position P1 means a position where it is presumed that the distal end of the sheath 31 and the inner surface of the duodenum come into contact with each other when the sheath 31 is advanced as it is.

The operator adjusts the position P1 by operating the endoscope so that the position P1 is within the range of the oral side projection Op and does not overlap with the opening Po. When the insertion portion of the endoscope is advanced or retracted, the insertion portion is bent in the vertical direction of the image, or the raising table is operated, the sheath 31 moves in the vertical direction in the image. When the insertion portion of the endoscope is twisted or the insertion portion is bent in the left-right direction of the image, the sheath 31 moves in the left-right direction in the image. By appropriately combining these operations, the position of the sheath 31 in the image can be changed and the position P1 can be adjusted.

After adjusting the position P1, the distal end of the sheath 31 may be brought into contact with the position P1. If the sheath 31 is brought into contact with the oral side projection on the oral side at this timing, there is an advantage that the sheath position is less likely to shift when the sheath is aligned in the ultrasound image described later.

Since the opening Po is closed most of the time, it cannot be imaged by an ultrasound image. In addition, the resolution of the current ultrasound image is not so good that the oral side projection can be accurately imaged. Therefore, the above-mentioned aligning step in the optical image is required.

In FIG. 6, a preferable range of the position P1 is shown as an area A1. The area A1 is within the range of the oral side projection Op, which is a portion of the duodenal papilla raised from the inner wall of the duodenum on the oral side of the opening Po. The opening Po is not included in the oral side projection Op. If the position where the puncture device is punctured shifts to the left, right, up or down with respect to the area A1, the possibility of penetrating the duodenum and protruding into the abdominal cavity or stimulating the opening increases. By adjusting the position P1 within the area A1, the puncture device can be reliably punctured into the oral side projection and the risk described above can be reduced.

On the right side of FIG. 6, the cross-sectional shape of the oral side projection Op and its surroundings is schematically shown. In a case where the optical image has an assist function for displaying the protruding direction of the needle in the optical image, the position P1 can be adjusted in the area A1 by using this as a guide. In this case, the position P1 can be adjusted within the area A1 without having the distal end of the puncture device 30 protrude from the exit of the treatment device channel.

Next, while observing the ultrasound image by the ultrasound vibrator 13, moving the ultrasound vibrator 13, and changing the scanning surface from which the image is acquired, the operator selects the scanning surface in which the bile duct is imaged at the position closest to the duodenal papilla and holds the ultrasound vibrator 13.

During the procedure, both the optical image and the ultrasound image may be displayed at all times, or only one may be displayed while switching appropriately.

Figure 7:
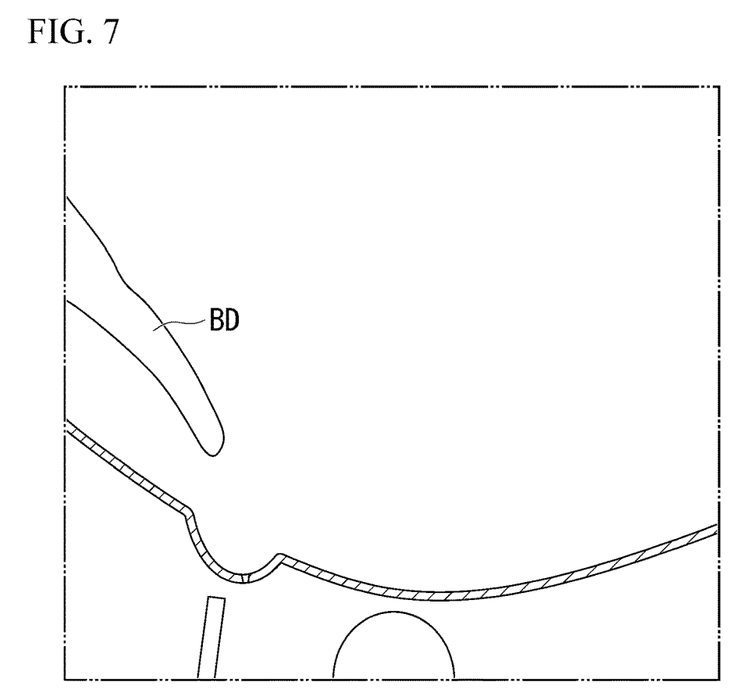
FIG. 7 is a diagram showing an example of an ultrasound image.
Figure 8:
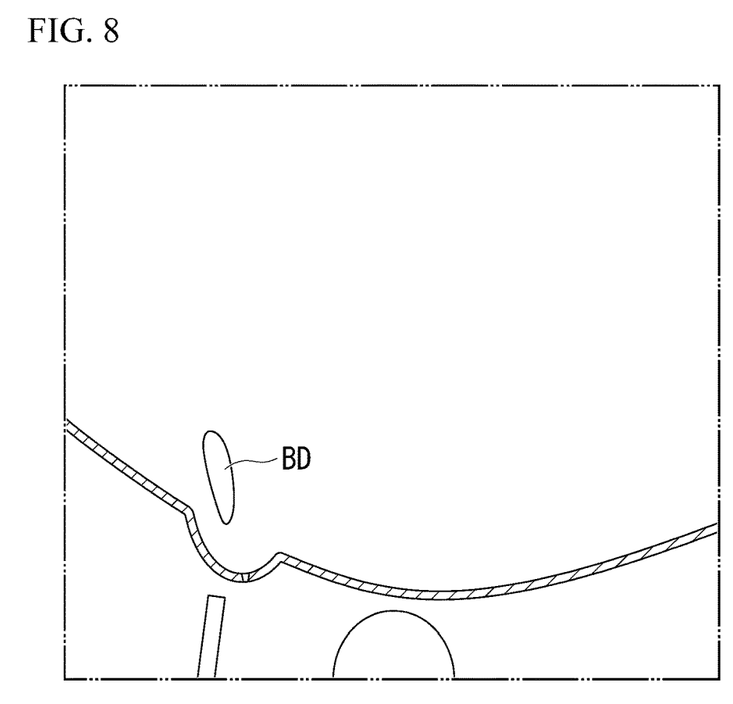
FIG. 8 is a diagram showing an example of an ultrasound image.

For example, in the ultrasound image shown in FIG. 7 and the ultrasound image shown in FIG. 8, compared with the bile duct BD imaged in FIG. 7, the lower bile duct BD closer to the duodenal papilla is imaged in FIG. 8. In such a case, the operator selects the scanning surface corresponding to FIG. 8.

As described above, the oral side projection is usually not accurately imaged in the ultrasound image, but in the drawings of the present specification, the oral side projection is shown in order to make it easier to understand the positional relationship with the bile duct.

The scanning surface is changed by operating the endoscope while taking care that the position P1 (the distal end of the sheath when the sheath 31 is in contact with the oral side projection) does not deviate from the area A1, and changing the emission direction of the ultrasound waves. Specifically, the scanning surface is adjusted by appropriately combining the advance/retreat and the twist (rotation) of the endoscope, and the bending of the curved portion of the endoscope in the vertical/horizontal directions.

The common duct after the bile duct and pancreatic duct merge is difficult to be recognized on ultrasound images because the sphincter muscle of the duodenal papilla is narrowed or closed due to contraction most of the time. However, since the bile duct on a bit upstream side of the confluence of the bile duct and the pancreatic duct remains open, it can be visually recognized by an ultrasound image. Although the bile duct has a complex three-dimensional run, the lowermost part on the ultrasound image, which is the closest to the duodenal papilla, can be identified by the above steps.

Figure 9:
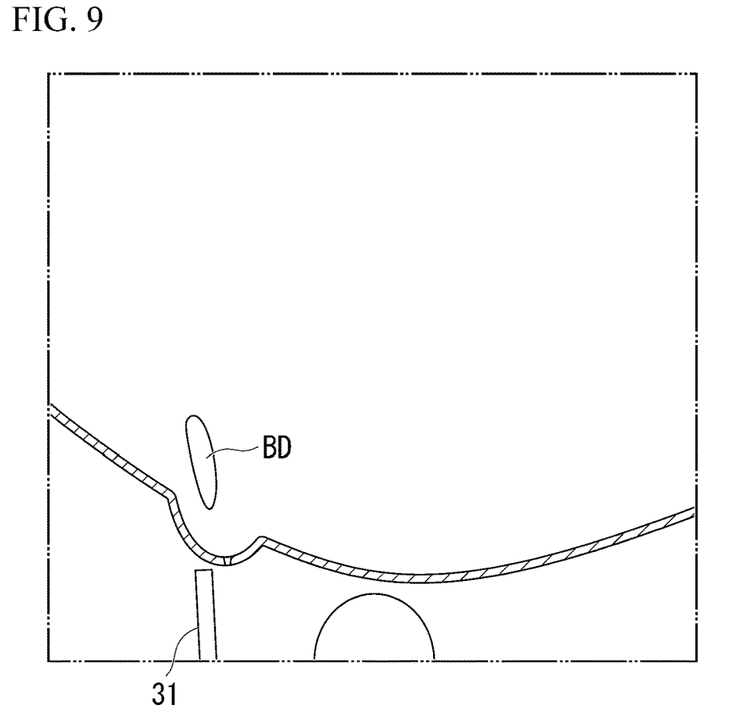
FIG. 9 is a diagram showing one process of the access route forming method according to an embodiment.

The operator operates the sheath 31 while observing the ultrasound image, maintaining the position of the scanning surface so that the position P1 (the distal end of the sheath when the sheath 31 is in contact with the oral side projection) does not deviate from the area A1 and the lowermost part of the bile duct can be imaged, and positions the lowermost part of the bile duct BD on the extension line of the sheath 31 as shown in FIG. 9. Specifically, it is adjusted by appropriately combining the minute advance/retreat and twist (rotation) of the endoscope, bending of the curved portion of the endoscope in the vertical and horizontal directions, and raising the rising table in a state where there is a rising table. Since water is stored in the duodenum, the sheath 31 is in a state where it can be imaged on an ultrasound image. Similarly, in a state where the ultrasound image has an assist function for displaying the needle protruding direction, the angle of the sheath with respect to the tissue may be adjusted so that the lowermost portion of the bile duct BD is positioned on the display of the needle protruding direction. At this time, the angle formed by the longitudinal axis of the sheath 31 and the extending direction of the bile duct BD on the downstream side of the bile duct is preferably as small as possible. As the angle becomes smaller, the longitudinal axis of the sheath 31 and the extending direction of the bile duct become closer to parallel.

The operator confirms on the ultrasound image that there is no pancreatic duct between the distal end of the sheath and the lowermost part of the bile duct on its extension line. In addition, the operator puts the endoscope in Doppler mode and confirms on ultrasound images that there are no blood vessels between the distal end of the sheath and the lowermost part of the bile duct. In a case where there are blood vessels, a predetermined color such as red or blue indicating blood flow is displayed on the ultrasound image.

In a case where there is either a pancreatic duct or a blood vessel between the distal end of the sheath and the lowermost part of the bile duct, if the needle tube is protruded as it is, there is a high possibility that the needle tube will pierce the pancreatic duct or blood vessel, so the position P1 is changed under optical observation, and the above procedure is performed again.

Either the presence or absence of the pancreatic duct or the presence or absence of the blood vessel may be confirmed first.

Figure 10:
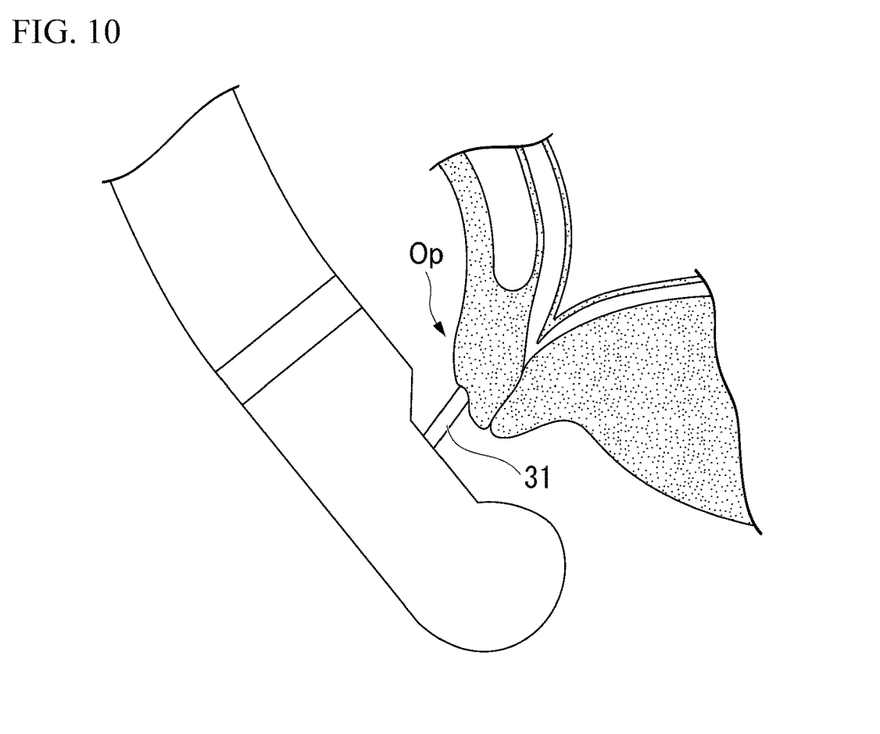
FIG. 10 is a diagram showing one process of the access route forming method according to an embodiment.

By the above process, the piercing angle of the needle tube into the oral side projection, that is, the path for advancing the needle tube 33 within the tissue of the oral side projection is determined. The operator may advance the sheath 31 while maintaining the position and orientation of the endoscope under optical observation, bring the distal end of the sheath 31 close to the oral side projection, and lightly contact the sheath 31 as shown in FIG. 10. By this operation, the distal end of the sheath 31 comes into contact with the oral side projection Op approximately at the position P1 or in the vicinity of the position P1.

As described above, when the distal end of the sheath 31 is brought into contact with the position P1 before positioning in the ultrasound image, this operation is not necessary.

Figure 11:
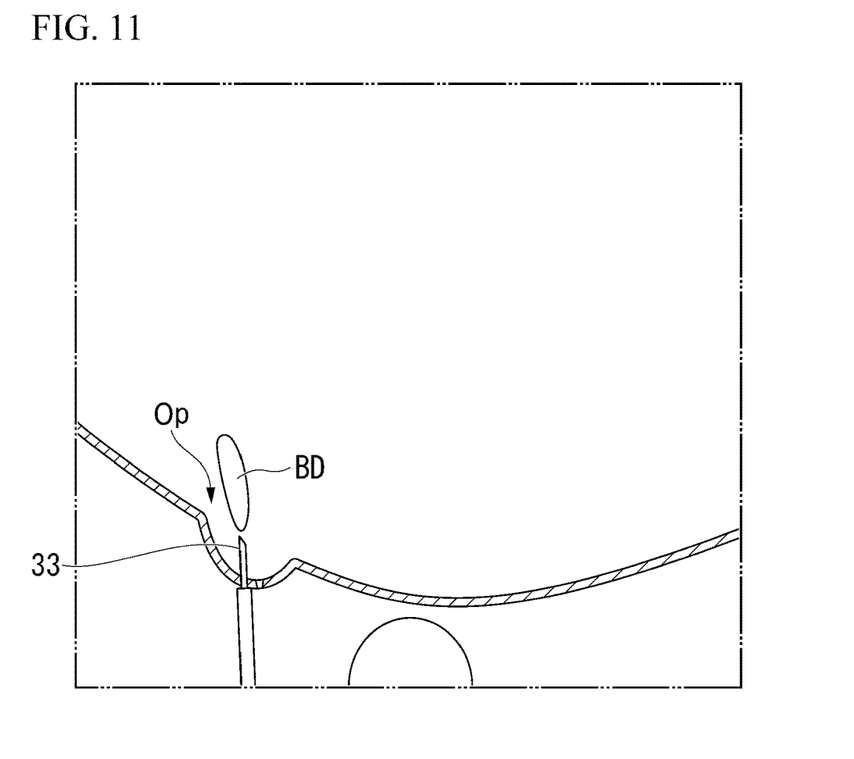
FIG. 11 is a diagram showing one process of the access route forming method according to an embodiment.

Subsequently, the operator operates the operation part 32 of the puncture device 30 under ultrasound observation to protrude the needle tube 33 from the sheath 31. As shown in FIG. 11, the protruding needle tube 33 pierces the oral side projection Op. When the needle tube 33 is further advanced, the needle tube 33 advances in the tissue of the oral side projection Op toward the upstream side of the bile duct BD, and approaches the lowermost part of the bile duct BD without exiting the abdominal cavity. When the needle tube 33 pierces the bile duct BD and the tip of the needle tube 33 reaches the inside of the bile duct BD, the operator stops the advance of the needle tube 33 and fixes it so as not to move with respect to the sheath 31.

If necessary, it may be confirmed by a method other than the ultrasound image whether or not the tip of the needle tube 33 is in the bile duct. In particular, an exemplary example of the method is as follows:

inject a contrast medium through the needle tube 33 and perform X-ray fluoroscopy;

insert a guide member (described later) into the needle tube 33 and protrude it from the needle tube 33 to check its behavior; or suction from the needle tube 33 and check if bile is suctioned.

The needle tube 33 inserted into the oral side projection reaches the bile duct without exiting the abdominal cavity and without contacting any of the openings of the duodenal papilla, the pancreatic duct ostium, the common duct, the pancreatic duct, and large blood vessels. That is, the tunnel formed in the duodenum by the needle tube 33 is a tunnel that connects together the inside of the duodenum and the bile duct without going out to the abdominal cavity and stimulating each of the above-mentioned sites. Since the needle duct 33 is stuck in the bile duct from the downstream side to the upstream side of the bile duct, it advances toward the upstream side when further advanced.

Figure 12:
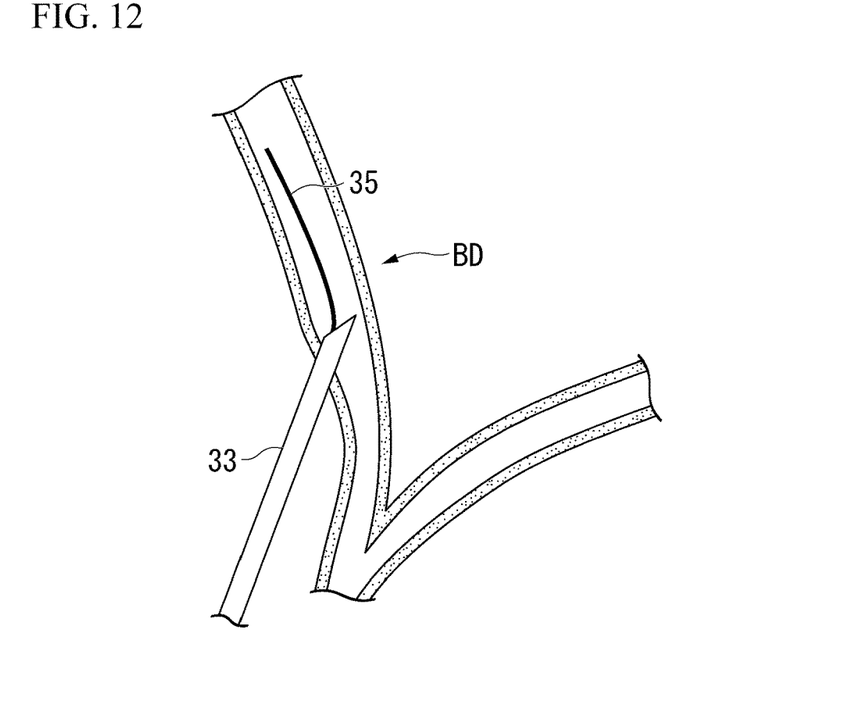
FIG. 12 is a diagram showing one process of the access route forming method according to an embodiment.

The operator inserts the guide member (treatment device) 35 into the needle tube 33 from a proximal end of the puncture device 30, advances the inside of the needle tube, and protrudes it from the tip of the needle tube 33. A guide wire is typical as the guide member in the present embodiment. As shown in FIG. 12, the guide member 35 extends in the bile duct BD from the downstream side to the upstream side. The guide member 35 may have at least a distal end that is reflected in an X-ray image or an ultrasound image.

When the guide member 35 is sufficiently placed in the bile duct BD, the operator removes the puncture device 30 leaving the guide member 35. This forms an access route from the duodenum to the bile duct. This access route does not irritate these sites because it does not touch the opening of the duodenal papilla, the pancreatic duct ostium, or the common duct.

After forming the access route, various treatments can be performed by introducing the distal ends of various treatment devices into the bile duct via the access route along the guide member 35. Some of them are shown below.

A contrast catheter is inserted into the bile duct along the guide member 35, and ERCP is performed.

A basket-type treatment device is inserted into the bile duct along the guide member 35 to treat intrabile duct stones.

A treatment device having a balloon is inserted into the bile duct along the guide member 35 to treat intrabile duct stones and dilate a narrowed portion of the bile duct.

A biopsy forceps is inserted into the bile duct along the guide member 35, and tissues such as the bile duct used for definitive diagnosis of malignant tumors and the like are collected.

A stent delivery system is inserted into the bile duct along the guide member 35 and the stent is placed in the bile duct.

When performing the procedure, the access route may be expanded by performing endoscopic sphincterotomy (EST) or endoscopic papillary balloon dilatation (EPBD) as needed. Further, the access route may be extended by combining EST and EPBD.

As described above, according to the present embodiment, the route from within the duodenum to access the bile duct without touching the opening of the papilla of the duodenal papilla, the pancreatic duct ostium, and the common duct can be formed, with significantly reduced risk of intestinal perforation and major bleeding. As a result, various treatments for the bile duct can be performed without stimulating the opening, the pancreatic duct ostium, and the common duct, and the occurrence of complications due to these stimuli can be significantly reduced. These advantages cannot be realized by the technique described in Published Japanese Translation No. 2013-507185 of the PCT International Publication, in which it is assumed that a stent is placed, the needle penetrates the duodenum and enters the abdominal cavity.

In addition, by combining optical observation with an endoscope and ultrasound observation, the path of the needle from the oral side projection to the bile duct can be easily identified without passing through a large blood vessel or pancreatic duct. Therefore, compared to the conventional ERCP, it does not require advanced skills and can be easily performed by many operators.

As another method for forming an access route from the oral side projection to the bile duct, a method of incising the oral side projection under optical observation is known. This method does not provide any information about the presence or absence of the abdominal cavity or the presence or absence of blood vessels or pancreatic ducts in the incised tissue. Therefore, the possibility of unintended perforation or bleeding cannot be reduced. A low-risk route from the oral side projection to the bile duct can be realized only by combining the determination of the insertion position under optical observation and the determination of the piercing angle under ultrasound observation as in the present embodiment.

In the access route forming method of the present embodiment, the details of each process and the device used can be changed in various ways. Some of them will be described below.

(Curved Mode of the Endoscope Insertion Part)

Figure 13:
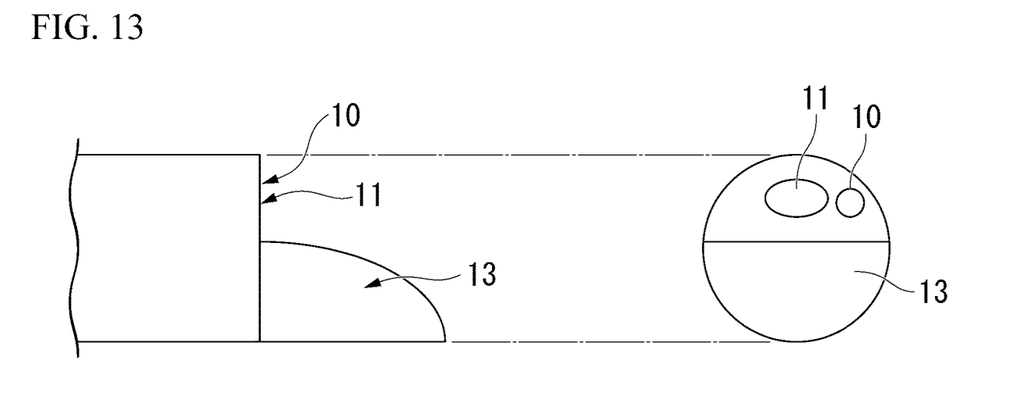
FIG. 13 is a diagram showing a distal end portion of an endoscope used in a modified mode.
Figure 14:
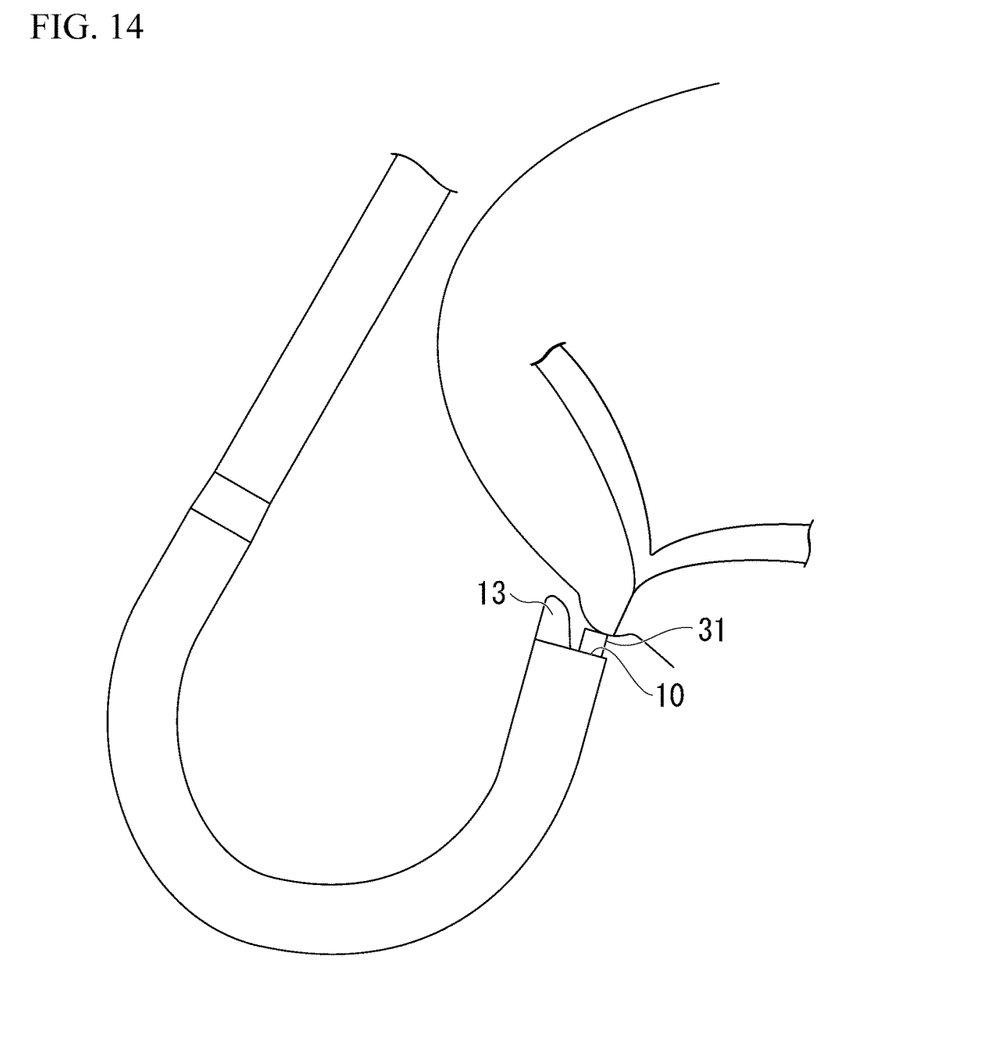
FIG. 14 is a diagram showing one process of an access route forming method according to the modified mode.

In the above description, as shown in FIG. 4 and the like, the side-view type endoscope is curved so that the side where the optical observation part 10 is located is inside the curve. This embodiment has an advantage that the orientation of the endoscope can be easily stabilized in the duodenum and optical observation as shown in FIG. 6 can be easily performed. As another embodiment, when a direct-view type endoscope in which the optical observation part 10 is provided at the distal end portion is used as shown in FIG. 13, the endoscope may be curved in one direction by about 180° and inverted as shown in FIG. 14. At this time, the endoscope may be curved so that the side with the optical observation part 10 is on the outside of the curve, or the side with the optical observation part 10 may be curved on the inside of the curve. In this case, the sheath 31 of the puncture device protruding from the outlet 11 can be inserted into the oral side projection without being strongly bent by a rising table or the like. As a result, the resistance when moving the sheath or needle tube of the puncture device back and forth is reduced, and the operation of the puncture device becomes smooth.

(Sheath Approach to the Oral Side Projection)

When the distal end of the sheath brought close to the oral side projection is brought into contact with the oral side projection, the sheath in contact with the oral side projection may be further pushed in, and the distal end of the sheath may be sunk into the oral side projection. In this case, since there is a tissue of the oral side projection around the distal end of the sheath, by bringing the ultrasound vibrator into contact with the duodenum wall, the distal end of the sheath can be imaged in an ultrasound image without storing water in the duodenum. As a result, it becomes possible to execute the access route forming method by omitting the step of storing water.

(Device Configuration)

In the above description, a hollow needle tube was used as the needle to pierce the oral side projection.

Figure 15:
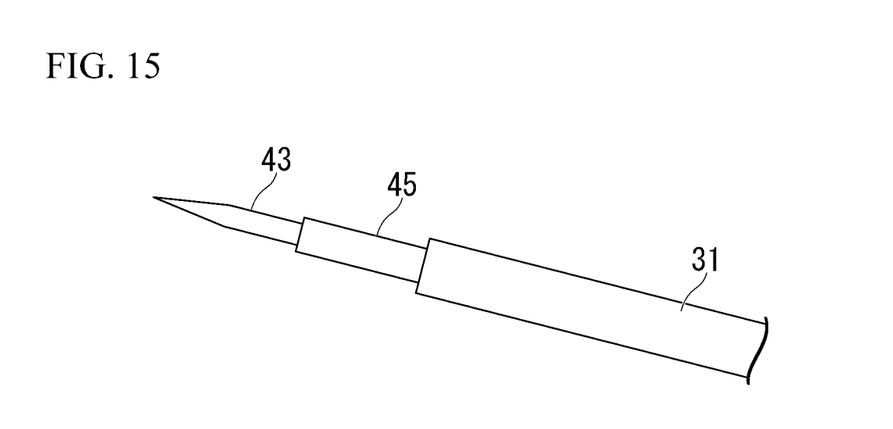
FIG. 15 is a diagram showing another example of the puncture device.

As another embodiment, a non-tubular solid needle 43 as shown in FIG. 15 may be used. In this case, as the guide member, a guide tube 45 having an inner diameter larger than the outer diameter of the needle 43 and an outer diameter smaller than the inner diameter of the sheath 31 can be used. The outer diameter of the guide tube 45 is small enough to pass through the guide wire lumen of the treatment device to be introduced later.

In the above description, an endoscope in which an ultrasound vibrator is attached to the insertion portion is used. As another embodiment, an ultrasound probe (hereinafter referred to as "insertion probe") equipped with an ultrasound vibrator having a size that can be passed through the treatment device channel of the endoscope may be combined with an endoscope capable of only optical observation, to execute the access route formation method.

In this case, a duodenal endoscope is inserted into the luminal organ through the patient's mouth or nose, and the distal end is moved to the vicinity of the duodenal papilla. Next, the duodenal papilla is imaged in the field of view of the optical observation part of the duodenal endoscope. When imaging the duodenal papilla in the field of view, it is desirable to position the duodenal papilla in front (center) of the optical image.

Next, the operator inserts the insertion probe into the treatment device channel from the entrance of the treatment device channel provided in the operation part of the endoscope.

When inserting the insertion probe into the endoscopic channel, the operator positions the distal end of the insertion probe near the exit of the treatment instrument channel. When the endoscope has the raising table, the raising table may be kept upright when the insertion probe is inserted, and the insertion probe may be inserted until the distal end of the insertion probe reaches the raising table. Further, when the distal end of the insertion probe reaches the vicinity of the raising table, the operation portion of the insertion probe may be attached to the entrance of the treatment device channel and fixed.

The operator then operates the endoscope and the insertion probe to position the distal end of the insertion probe within the field of view of the optical observation part.

Figure 16:
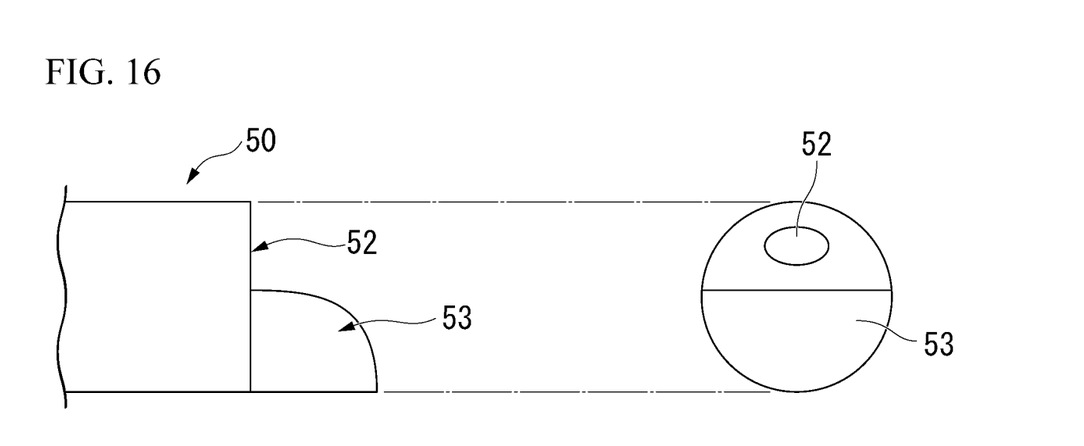
FIG. 16 is a diagram showing a distal end portion of an insertion probe according to the modified mode.

FIG. 16 shows the distal end of the insertion probe 50. The insertion probe 50 has a structure in which an ultrasound vibrator 53 is attached to the distal end of an elongated insertion portion. A channel extends in the longitudinal direction at the insertion portion, and an outlet 52 opens at the distal end.

The operator adjusts the position P1 by operating the endoscope so that the position P1 is within the range of the oral side projection Op and does not overlap with the opening Po. The position P1 at this time is a position on the surface of the duodenum that coincides with the extension line of the longitudinal axis of the insertion probe 50. When the insertion portion of the endoscope is advanced or retracted, the insertion portion is curved in the vertical direction of the image, or the raising table is operated, the distal end of the insertion probe 50 moves in the vertical direction in the image. When the insertion portion of the endoscope is twisted or the insertion portion is curved in the left-right direction of the image, the distal end of the insertion probe 50 moves in the left-right direction in the image. By appropriately combining these operations, the position of the distal end of the insertion probe in the image can be changed and the position P1 can be adjusted.

After adjusting the position P1, the ultrasound vibrator 53 at the distal end of the insertion probe 50 is lightly brought into contact with the oral side projection Op.

The insertion probe 50 has an assist function of displaying the protruding direction of the needle on the ultrasound image. The operator confirms the bile duct and the pancreatic duct with the ultrasound image acquired by the insertion probe 50, and identifies the bile duct from the difference in direction (running).

Next, the operator moves the ultrasound vibrator 53 while viewing the ultrasound image by the ultrasound vibrator 53 to change the scanning surface from which the image is acquired in various ways, and selects the scanning surface in which the bile duct is imaged closest to the duodenal papilla and holds the ultrasound vibrator 53. Specifically, the scanning surface is adjusted by appropriately combining the advance/retreat or the twist (rotation) of the endoscope, the bending of the curved portion of the endoscope in the vertical/horizontal directions, and the operation of the raising table.

In addition, the display of the assist function is adjusted to pass through the lowermost part of the bile duct. The specific operation is almost the same as the adjustment of the scanning surface described above.

Further, as in the above-described embodiment, the following is performed.

Check that there are no blood vessels on the assist display in Doppler mode for ultrasound observation. (This step can be omitted.)

Check that there is no pancreatic duct on the assist display on the ultrasound image. Either the confirmation that there is no blood vessel or the confirmation that there is no pancreatic duct may be performed first.

Up to this point, the insertion route of the needle tube 33 is determined.

Figure 17:
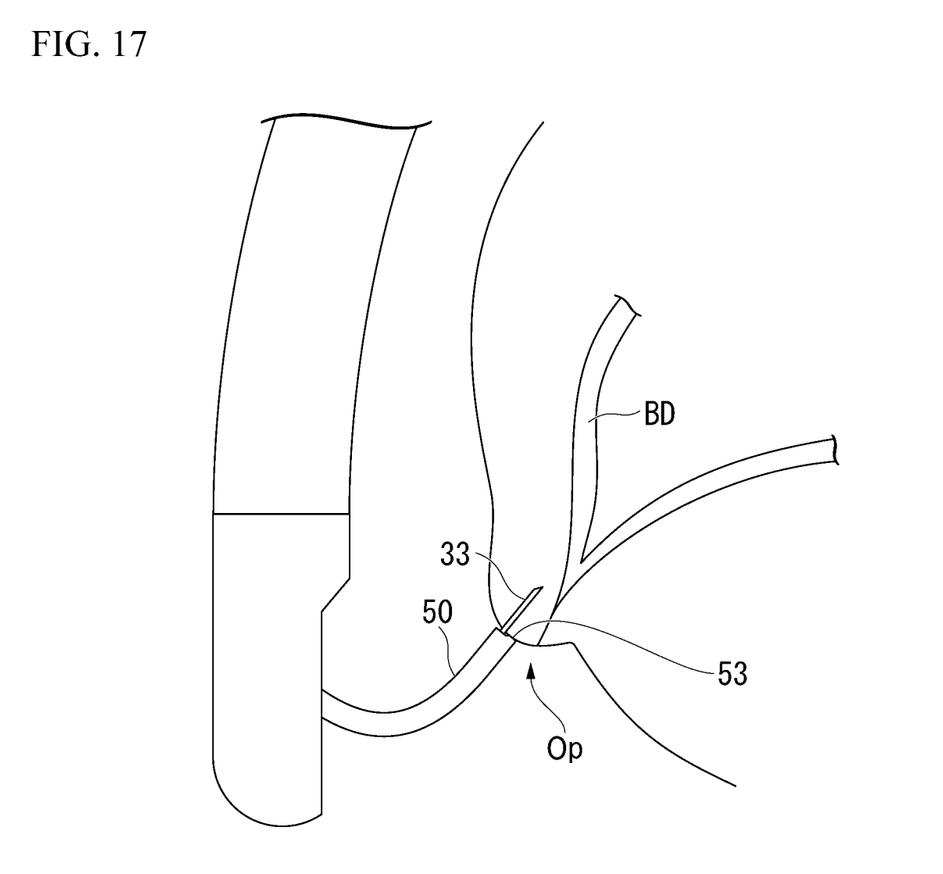
FIG. 17 is a diagram showing one process of the access route forming method according to the modified mode.

After determining the insertion route, the needle tube 33 is inserted into the oral side projection Op from the insertion probe 50 as shown in FIG. 17. Check the needle tip on the ultrasound image, and stop the needle when the needle tip reaches the inside of the bile duct BD.

The insertion portion of the insertion probe 50 may be provided with a mechanism capable of bending in advance or actively bending. In this way, as shown in FIG. 17, the insertion probe 50 protruding from the endoscope can be easily directed to retract towards the proximal end of the endoscope.

If necessary, confirm whether the needle tip has reached the inside of the bile duct by means other than the ultrasound waves described above. (This step can be omitted.)

Insert the guide member deep into the bile duct while checking it with an X-ray image or an ultrasound image. (At least the distal end of which is reflected in the X-ray image or ultrasound image is used as the guide member)

Remove the insertion probe 50 from the bile duct and scope, leaving the guide member.

Use the guide member as a guide to perform ERCP or the related procedure described above.

In this embodiment using the insertion probe 50, the ultrasound vibrator 53 is brought into contact with the oral side projection Op, and the above-mentioned assist function can be used, so that the step of storing water in the duodenum can be omitted. As a result, the procedure becomes simpler.

In this embodiment, the needle tube 33 may be attached to and integrated with the insertion probe 50.

Although the present invention has been described above using one embodiment and its modified mode, the technical scope of the present invention is not limited to the above-described embodiment. It is possible to change the combination of components, make various changes to each component, and delete them without departing from the spirit of the present invention.

What is claimed is:

1. A method for forming an access route to a bile duct, the method comprising:

introducing a needle into a duodenum;

piercing an oral side projection of a duodenal papilla with the needle, the oral side projection being located at an oral position other than an opening of the duodenal papilla;

forming a tunnel by progressing a tip of the needle into the bile duct, the tunnel being configured to allow communication between the duodenum and the bile duct; and inserting a treatment device into the tunnel.

2. The method according to claim 1, wherein the needle progresses in a tissue of the oral side projection toward an upstream side of the bile duct.

3. The method according to claim 1, wherein determining a position to be pierced by the needle by optical observation of the duodenal papilla and the needle, and determining a piercing angle of the needle by ultrasound observation of the duodenal papilla.

4. The method according to claim 3, further comprising:

introducing the needle into the duodenum while being passed through a sheath, and, in the optical observation, determining the position to be pierced by the needle on the basis of a position of the sheath.

5. The method according to claim 3, further comprising:

introducing the needle into the duodenum while being passed through a sheath, and determining the piercing angle so that the sheath is directed toward a lowermost part of the bile duct imaged in an ultrasound image.

6. The method according to claim 3, further comprising determining the piercing angle after determining the position.

7. The method according to claim 3, further comprising:

performing the optical observation using an endoscope provided with an optical observation part, performing the ultrasound observation using an insertion probe inserted into the endoscope, and introducing the needle into the duodenum via the insertion probe.

8. The method according to claim 3, further comprising:

performing the optical observation using an endoscope provided with an optical observation part, performing the ultrasound observation using an ultrasound vibrator provided in the endoscope, and introducing the needle into the duodenum via the endoscope.

9. The method according to claim 8, wherein a visual field direction of the optical observation part is provided 90° or more in a distal end direction relative to an endoscope axis, the endoscope has a raising table capable of directing the needle protruding from the endoscope at 90° or more in the distal end direction relative to the endoscope axis, and by piercing the needle into the oral side projection in a state where the needle is pointed 90° or more in the distal end direction relative to the endoscope axis using the raising table, the needle advances within a tissue of the oral side projection towards the upstream side of the bile duct.

10. The method according to claim 3, wherein the needle is introduced into the duodenum via an endoscope provided with an optical observation part, and the endoscope is held in the duodenum in a state where a distal end portion provided with the optical observation part is inverted.

11. The method according to claim 4, wherein when a distal end of the sheath contacts the oral side projection, the needle is configured to advance.

12. The method according to claim 3, wherein the ultrasound observation is performed when water is stored in the duodenum.

* * * * *